US009102417B1

(12) United States Patent
Young

(10) Patent No.: US 9,102,417 B1
(45) Date of Patent: Aug. 11, 2015

(54) HEALTH MONITORING SYSTEM FOR A VEHICLE

(75) Inventor: Donald R. Young, Tulalip, WA (US)

(73) Assignee: THE BOEING COMPANY, Chicago, IL (US)

(*) Notice: Subject to any disclaimer, the term of this patent is extended or adjusted under 35 U.S.C. 154(b) by 480 days.

(21) Appl. No.: 12/965,527

(22) Filed: Dec. 10, 2010

(51) Int. Cl.
*G08B 21/00* (2006.01)
*B64D 45/00* (2006.01)

(52) U.S. Cl.
CPC .......... *B64D 45/00* (2013.01); *B64D 2045/004* (2013.01); *B64D 2045/0055* (2013.01); *B64D 2045/0085* (2013.01)

(58) Field of Classification Search
CPC ................ B64D 2045/004; B64D 2045/0055; B64D 2045/0085; B64D 2013/00; B64D 2013/0637; G05D 1/0061
USPC ........... 340/945, 963; 128/204.23; 701/11, 14
See application file for complete search history.

(56) References Cited

U.S. PATENT DOCUMENTS

| | | | | |
|---|---|---|---|---|
| H1039 | H * | 4/1992 | Tripp et al. | 128/206.28 |
| 5,213,099 | A * | 5/1993 | Tripp, Jr. | 600/324 |
| 8,356,595 | B2 * | 1/2013 | Schaeffer et al. | 128/204.29 |
| 2002/0148470 | A1 * | 10/2002 | Blue et al. | 128/204.22 |
| 2003/0034902 | A1 * | 2/2003 | Dickau | 340/945 |
| 2003/0048203 | A1 * | 3/2003 | Clary et al. | 340/945 |
| 2004/0206353 | A1 * | 10/2004 | Conroy, Jr. | 128/204.23 |
| 2007/0118301 | A1 * | 5/2007 | Andarawis et al. | 702/33 |
| 2007/0236366 | A1 * | 10/2007 | Gur et al. | 340/945 |
| 2010/0174424 | A1 * | 7/2010 | Cornell et al. | 701/9 |

OTHER PUBLICATIONS

Conroy et al., "Oxygen and Hypoxemia", The Magazine for the Instrument Pilot, Retrieved Nov. 11, 2010, pp. 1-2. http://www.ifr-magazine.com/oxygen-and-hypoxemia.html.
Furgang, "Choosing a Portable Aviation Oxygen System for Your Aircraft", Air-King, Retrieved Nov. 11, 2010, pp. 1-4. www.deltaoxygensystems.com/id83.html.
"Pilot Vision", Federal Aviation Administration, Retrieved Nov. 11, 2010, pp. 1-9. http://www.faa.gov/pilots/safety/pilotssafetybrochures/media/pilot_vision.pdf.

* cited by examiner

*Primary Examiner* — Vernal Brown
*Assistant Examiner* — Hongmin Fan
(74) *Attorney, Agent, or Firm* — Yee & Associates, P.C.

(57) ABSTRACT

Method and apparatus for monitoring a vehicle. An apparatus comprises a sensor system and a computer system. The sensor system is associated with a number of human operators of a vehicle and a number of components in the vehicle. The sensor system is configured to generate physiological data for the number of human operators. The computer system is configured to receive the physiological data; determine whether the physiological data is within a level for a desired level of performance for operating the vehicle based on a policy; and perform a number of actions to maintain the desired level of performance for operating the vehicle in response to the physiological data not being within the level for the desired level of performance.

21 Claims, 9 Drawing Sheets

HEALTH MONITORING SYSTEM FOR A VEHICLE

BACKGROUND INFORMATION

1. Field

The present disclosure relates generally to vehicles and, in particular, to a health monitoring system for a vehicle. Still more particularly, the present disclosure provides a method and apparatus for maintaining a desired level of performance in a vehicle using a health monitoring system.

2. Background

A transportation environment may be land, sea, air, outer space, of a combination of these. In each of these types of transportation environments, undesired operating conditions may be present for the vehicle. These undesired operating conditions may result from various sources. These sources may include, for example, vehicle systems not operating as expected or crew members not performing operations as expected. Vehicle system may not operate as expected if oil pressures are not as high as desired on a land-based vehicle. Another example of a system not operating as expected is if a structure on an aircraft does not carry a desired load.

In avoiding undesired operating conditions for vehicles, monitoring systems may be used in vehicles. These monitoring systems monitor systems and structures in the vehicle. These monitoring systems may assess the "health" of the systems and structures in the vehicle. Further, these monitoring systems may provide alerts to an operator of the vehicle when a condition occurs in which the health of a system or structure does not allow it to operate as expected or may not operate as expected in the near future. These types of monitoring systems are also referred to as health monitoring systems.

With respect to vehicle operators such as pilots, regulations are present to set the hours that pilots may operate aircraft and how much rest is needed in between flights. Additionally, regulations are also present to identify physical conditions needed to operate an aircraft. Records may be checked to ensure that pilots operate aircraft within the regulations. Further, tests also may be performed to check pilots to determine whether they meet regulations regarding physical conditions.

With monitoring systems for vehicles and regulations for operators of vehicles in place, the occurrence of undesired operating conditions for a vehicle may be reduced or avoided. However, with operators of vehicles, the ability of an operator to control or manage a vehicle may change during operation of the vehicle. These types of changes may lead to undesired operating conditions for the vehicle.

Accordingly, it would be advantageous to have a method and apparatus which takes into account one or more of the issues discussed above, as well as possibly other issues.

SUMMARY

In one advantageous embodiment, an apparatus comprises a sensor system and a computer system. The sensor system is associated with a number of human operators of a vehicle and a number of components in the vehicle. The sensor system is configured to generate physiological data for the number of human operators. The computer system is in communications with the sensor system and is configured to receive the physiological data; determine whether the physiological data is within a level for a desired level of performance for operating the vehicle based on a policy; and perform a number of actions to maintain the desired level of performance for operating the vehicle in response to the physiological data not being within the level for the desired level of performance.

In another advantageous embodiment, a health monitoring system for an aircraft comprises a sensor system and a computer system. The sensor system is associated with a number of components in the aircraft and is configured to be associated with a number of human operators of the aircraft and the number of components in the aircraft. The sensor system is configured to generate physiological data for the number of human operators and data for the number of components. The computer system is configured to receive the physiological data and the data from the number of components; determine whether the physiological data of a human operator in the number of human operators is within a level for a desired level of performance of the human operator for operating the aircraft based on a profile for the human operator in a number of profiles in which each profile in the number of profiles corresponds to a particular human operator in the number of human operators; and perform a number of actions to maintain the desired level of performance for operating the aircraft in response to the physiological data not being within the level for the desired level of performance.

In another advantageous embodiment, a method is present for monitoring a vehicle. Physiological data is received at a computer system from a sensor system associated with a number of human operators of the vehicle and a number of components in the vehicle, wherein the physiological data includes a number of physiological data for the number of human operators. The computer system determines whether the physiological data is within a level for a desired level of performance for operating the vehicle based on a policy; and the computer system performs a number of actions to maintain the desired level of performance for operating the vehicle in response to the number of physiological data not being within the level for the desired level of performance.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
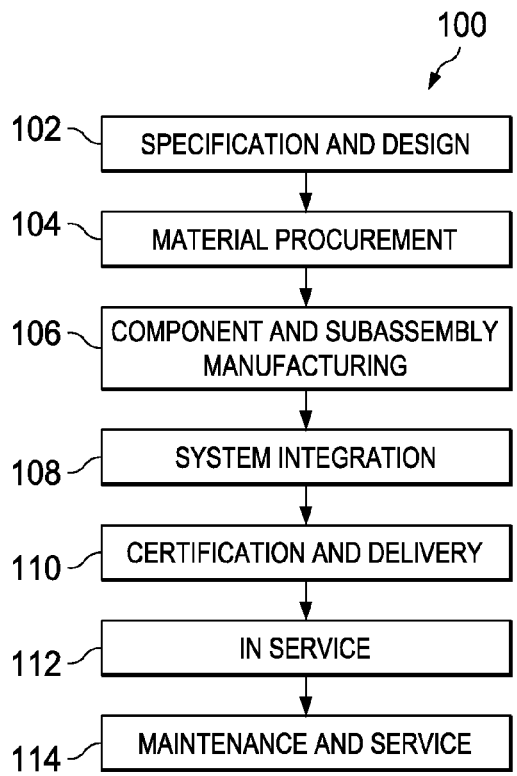
FIG. 1 is an illustration of an aircraft manufacturing and service method in accordance with an advantageous embodiment.
Figure 2:
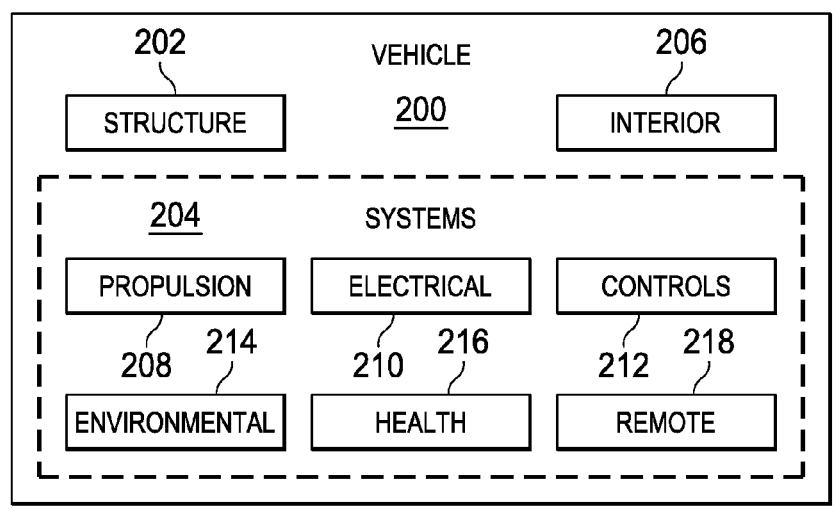
FIG. 2 is an illustration of a vehicle in which an advantageous embodiment may be implemented.

Referring more particularly to the drawings, embodiments of the disclosure may be described in the context of vehicle manufacturing and service method 100 as shown in FIG. 1 and vehicle 200 as shown in FIG. 2. Turning first to FIG. 1, an illustration of a vehicle manufacturing and service method is depicted in accordance with an advantageous embodiment. During pre-production, vehicle manufacturing and service method 100 may include specification and design 102 of vehicle 200 in FIG. 2 and material procurement 104.

During production, component and subassembly manufacturing 106 and system integration 108 of vehicle 200 in FIG. 2 takes place. Thereafter, vehicle 200 in FIG. 2 may go through certification and delivery 110 in order to be placed in service 112. While in service 112 by a customer, vehicle 200 in FIG. 2 is scheduled for routine maintenance and service 114, which may include modification, reconfiguration, refurbishment, and other maintenance or service.

Each of the processes of vehicle manufacturing and service method 100 may be performed or carried out by a system integrator, a third party, and/or an operator. In these examples, the operator may be a customer. For the purposes of this description, a system integrator may include, without limitation, any number of vehicle manufacturers and major system subcontractors; a third party may include, without limitation, any number of vendors, subcontractors, and suppliers; and an operator may be an airline, leasing company, military entity, service organization, and so on.

With reference now to FIG. 2, an illustration of a vehicle is depicted in which an advantageous embodiment may be implemented. In this example, vehicle 200 is produced by vehicle manufacturing and service method 100 in FIG. 1 and may include structure 202, systems 204, and interior 206. Systems 204 may include one or more of propulsion 208, electrical 210, controls 212, environmental 214, health 216, and remote 218.

For example, when vehicle 200 takes the form of a land vehicle, structure 202 may comprise a frame, a number of wheels and a number of axles. Propulsion 208 may comprise a drive train, an engine, and a motor. Controls 212 may comprise rotatable wheels operably coupled to an operator device.

In the case of vehicle 200 being a surface ship, structure 202 may comprise a water-tight hull. Propulsion 208 may comprise a power plant; and controls 212 may comprise a steering mechanism such as a rudder or steerable propeller pods operably coupled to an operator device.

Structure 202 may comprise an airframe in an example when vehicle 200 is an aircraft. Propulsion 208 may comprise one or more jet engines. Controls 212 may comprise one or more adjustable wing surfaces operably coupled to an operator device.

For a spacecraft, structure 202 may comprise a capsule. Propulsion 208 may comprise a rocket. Controls 212 may comprise a number of maneuvering jets operably coupled to an operator device.

Of course, vehicle 200 may take other forms depending on the particular implementation. In these different illustrative examples, health 216 is a health monitoring system that may be used to monitor different parts of vehicle 200. In particular, one or more of the different advantageous embodiments may be implemented in or using health 216.

Apparatuses and methods embodied herein may be employed during at least one of the stages of vehicle manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A or item A and item B. This example also may include item A, item B, and item C or item B and item C.

In one illustrative example, components or subassemblies produced in component and subassembly manufacturing 106 in FIG. 1 may be fabricated or manufactured in a manner similar to components or subassemblies produced while vehicle 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments is one or more apparatus embodiments. A number of apparatus embodiments, method embodiments, or a combination thereof may be utilized while vehicle 200 is in service 112 and/or during maintenance and service 114 in FIG. 1. The use of a number of the different advantageous embodiments may substantially expedite the assembly of and/or reduce the cost of vehicle 200.

The different advantageous embodiments recognize and take into account a number of different considerations. For example, the different advantageous embodiments recognize and take into account that once a human operator takes control of a vehicle, indications of an inability of the human operator to adequately perform operations to operate the vehicle typically only come from communication with that human operator.

The different advantageous embodiments also recognize and take into account that an event may change the ability of a human operator to operate a vehicle. In some cases, the human operator may not recognize a change in ability to properly operate the vehicle.

For example, a pilot of an aircraft may be unable to perform operations as quickly as desired when the level of oxygen in the blood is too low. This situation may cause an undesired operating condition in the aircraft. In other words, the level of the oxygen in the blood of a pilot may not be within a level for the desired level of performance in operating the aircraft.

For example, a way point may be missed, inadvertent contact with the ground may occur, a change in altitude may not occur when planned, and other undesired situations may occur when the pilot is not performing at a desired level.

Figure 3:
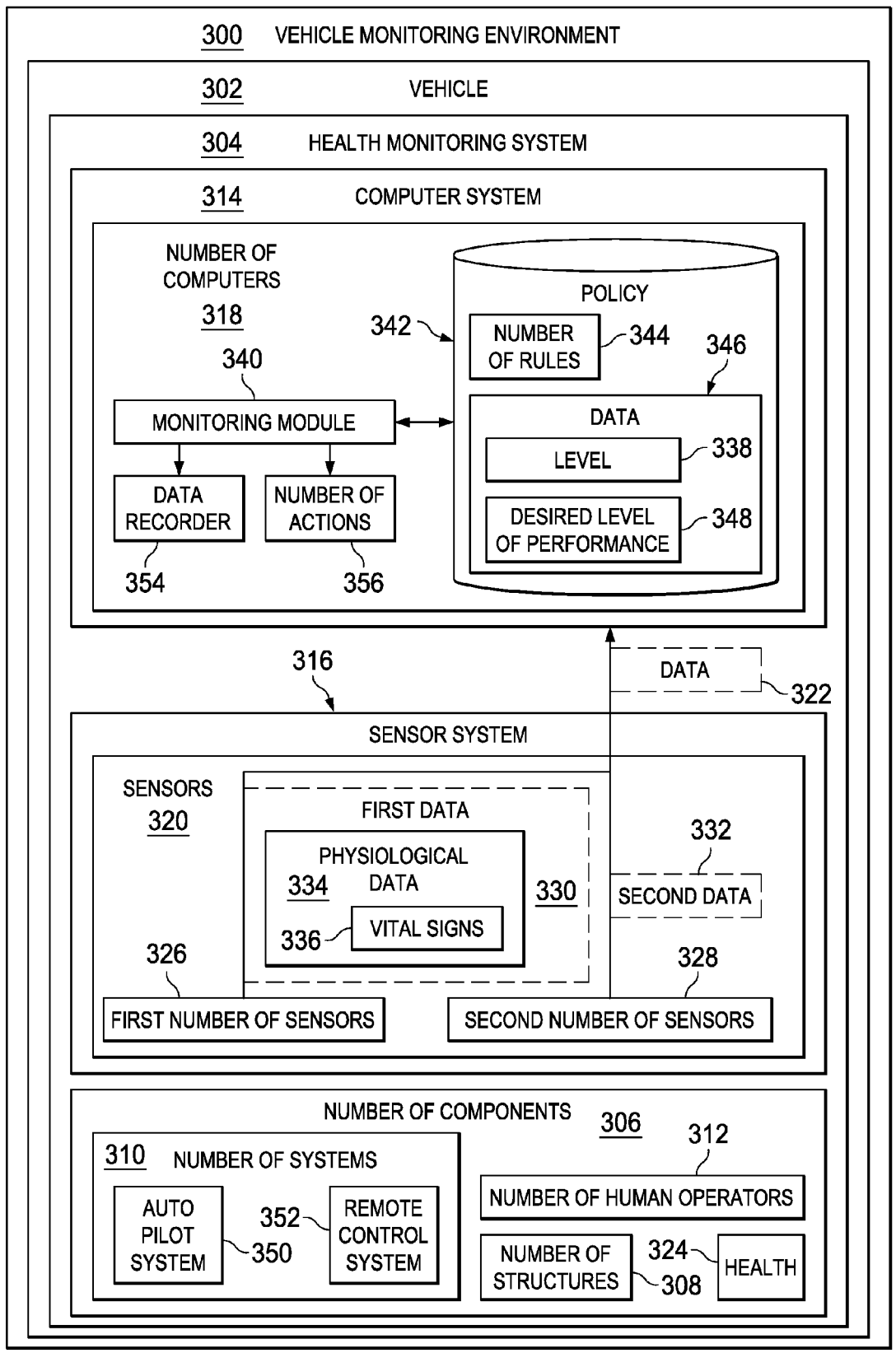
FIG. 3 is an illustration of a vehicle monitoring environment in accordance with an advantageous embodiment.

With reference now to FIG. 3, an illustration of a vehicle monitoring environment is depicted in accordance with an advantageous embodiment. Vehicle monitoring environment 300 is an example of an environment that may be implemented for use with vehicle 302. Vehicle 302 may be implemented using vehicle 200 in FIG. 2. For example, vehicle 302 may be an aircraft, a submarine, a personnel carrier, a tank, a train, an automobile, a bus, a spacecraft, a surface ship, and any other suitable vehicle.

Health monitoring system 304 may be used to monitor number of components 306 for vehicle 302. Health monitoring system 304 is an example of one implementation for health 216 in vehicle 200 in FIG. 2.

In these illustrative examples, number of components 306 includes, for example, without limitation, number of structures 308, number of systems 310, number of human operators 312, and other suitable types of components. Number of structures 308 may be, for example, a panel, a cabin in the vehicle, a cockpit, a stabilizer, a wheel, a landing gear, a wing, a frame, or some other suitable type of structure. Number of systems 310 may be, for example, without limitation, a hydraulics system, an environmental control system, a braking system, an electrical system, and other suitable types of systems.

In the depicted examples, number of human operators 312 are considered components that are monitored by health monitoring system 304. Number of human operators 312 is any person who may operate vehicle 302. Number of human operators 312 may include, for example, without limitation, a pilot, a co-pilot, a navigation officer, and other suitable types of human operators.

In these illustrative examples, health monitoring system 304 comprises computer system 314 and sensor system 316. Computer system 314 is number of computers 318. Sensor system 316 comprises sensors 320. A sensor in sensors 320 may be implemented using any sensor that measures a physical quantity and converts that measurement into a signal that may be used by computer system 314.

In these depicted examples, sensors 320 are associated with one or more of number of components 306. Sensors 320 generate data 322. Data 322 is sent to computer system 314. Computer system 314 uses data 322 to identify health 324 of number of components 306 within vehicle 302.

Health monitoring system 304 monitors health 324 of number of human operators 312 in addition to components typically monitored by health monitoring systems. By monitoring number of human operators 312, additional indications of whether vehicle 302 can be operated in a desired manner can be identified. By monitoring number of human operators 312, computer system 314 may be configured to determine whether number of human operators 312 is capable of performing operations within a desired level of performance to operate vehicle 302 in a desired manner. In these examples, data 322 includes data generated by sensors 320.

As depicted, first number of sensors 326 are associated with number of human operators 312. Second number of sensors 328 are associated with number of structures 308 and number of systems 310. In these illustrative examples, first number of sensors 326 generates first data 330 in data 322. Second number of sensors 328 generates second data 332 in data 322.

First data 330 may include any data used to identify health 324 of number of human operators 312 in these illustrative examples. As depicted, health 324 for number of human operators 312 provides an indication of an inability of number of human operators 312 to perform operations with regard to vehicle 302.

In the illustrative examples, first data 330 includes physiological data 334. Physiological data 334 is any data about number of human operators 312. Physiological data 334 may include, for example, vital signs 336 as well as other types of data regarding number of human operators 312.

Further, first data 330 also may include data other than physiological data 334. For example, first data 330 also may include measurements of the environment around number of human operators 312. Thus, first data 330 also may include data used to identify health 324 for number of systems 310 and/or number of structures 308.

In the depicted examples, second data 332 is data about number of systems 310 and number of structures 308. Second data 332 is data that may be used to identify health 324 for number of systems 310 and number of structures 308. Second data 332 may include at least one of positions of components, air information, responses to requests, measurements of temperature, load measurements, pressure, temperature gradients, data generated by components, and other suitable types of information that may be used to identify health 324 of number of systems 310 and number of structures 308.

Monitoring module 340 processes physiological data 334 as well as other data in first data 330. Monitoring module 340 also processes second data 332 received from second number of sensors 328 associated with other components in number of components 306, such as number of structures 308 and number of systems 310. In these illustrative examples, monitoring module 340 may be implemented using software, hardware, or a combination of the two.

Monitoring module 340 is configured to determine whether physiological data 334 is within level 338 for desired level of performance 348 for operating vehicle 302 based on policy 342. Desired level of performance 348 is a level of performance for number of human operators 312. In these examples, desired level of performance 348 may be different for different human operators within number of human operators 312 depending on the operations performed by number of human operators 312 in operating vehicle 302.

The identification of whether physiological data 334 is within level 338 is part of identifying health 324 for number of human operators 312 in these depicted examples.

In these illustrative examples, level 338 may take a number of different forms. For example, level 338 may be a number of thresholds, a number of ranges, or a combination of the two. Level 338 is selected as one that identifies health 324 of number of human operators 312 as being sufficient to operate vehicle 302 as expected or desired. In these examples, level 338 is selected such that number of human operators 312 has desired level of performance 348 for operating vehicle 302.

In these illustrative examples, desired level of performance 348 is for operating vehicle 302. Desired level of performance 348 may take a number of different forms. For example, desired level of performance 348 may include any operations performed by one or more of number of human operators 312 to operate vehicle 302.

These operations may include at least one of performing operations such as, for example, performing a takeoff, performing a landing, making a turn, calculating way points, changing altitude, changing speed, entering information, making decisions, changing a route, communicating with other human operators or remote locations, and any other suitable type of operation for operating vehicle 302. Desired level of performance 348 may include metrics, such as how quickly operations can be performed, how accurately operations can be performed, and other suitable types of metrics.

Policy 342 includes number of rules 344 that may be used to determine whether level 338 meets desired level of performance 348. Policy 342 also may include data 346. Additionally, policy 342 also may be used to determine whether number of systems 310 and number of structures 308 are performing as desired in identifying health 324 for these components.

In these illustrative examples, first data 330 is processed by monitoring module 340 using number of rules 344 and policy 342 to identify level 338. Then, monitoring module 340 determines whether physiological data 334 is within level 338 for desired level of performance 348 for operating vehicle 302. If physiological data 334 is not within level 338 for desired level of performance 348, monitoring module 340 is configured to perform number of actions 356.

In the depicted examples, number of actions 356 is performed to maintain desired level of performance 348 in operating vehicle 302. In other words, number of actions 356 may be such that number of human operators 312 may continue to operate vehicle 302 within desired level of performance 348. In the depicted example, number of actions 356 may include at least one of generating an alert, sending a message to a remote location, or some other suitable type of action. In one illustrative example, one human operator in number of human operators 312 may be unable to perform at desired level of performance 348. An alert or message may allow another human operator in number of human operators 312 to take over the operations performed by the human operator that is unable to perform at desired level of performance 348.

In other illustrative examples, number of actions 356 may include controlling number of systems 310 such that desired level of performance 348 is maintained in operating vehicle 302. In this example, desired level of performance 348 may require no actions performed by number of human operators 312 when number of actions 356 is performed.

For example, auto pilot system 350 or remote control system 352 in number of systems 310 may be controlled or activated by monitoring module 340 to operate vehicle 302. With auto pilot system 350, vehicle 302 may be operated with less or no operations being performed by number of human operators 312. With remote control system 352, operators in a remote location may operate vehicle 302 with less or no operations being performed by number of human operators 312.

In these illustrative examples, the determination is made as to whether level 338 is within desired level of performance 348 and also may include using second data 332 generated by second number of sensors 328 in monitoring at least one of number of structures 308 and number of systems 310 in number of components 306.

Second data 332 from number of structures 308 and number of systems 310 may be processed along with first data 330 for number of human operators 312. In this manner, health monitoring system 304 monitors both vehicle 302 and number of human operators 312 in vehicle 302. This data may be used to determine whether number of actions 356 may be needed to maintain desired level of performance 348 in operating vehicle 302. In the different illustrative examples, the results of decisions by monitoring module 340 may be recorded in a log or a database. This information is recorded in data recorder 354 in these depicted examples. Data recorder 354 is a storage device that may be used to record data 322 during the operation of vehicle 302. Determinations are made as to whether number of human operators 312 may be recorded in data recorder 354.

In some cases, only when physiological data 334 does not fall within level 338 for desired level of performance 348, physiological data may be recorded. For example, only instances in which oxygen levels are lower than level 338 may be recorded. As another example, if the pulse rates are less than a level set in level 338, then that instance is recorded in data recorder 354 in these examples. Physiological data 334 also may be recorded in data recorder 354.

In this manner, the different advantageous embodiments provide a capability to maintain desired level of performance 348 in operating vehicle 302.

The illustration of monitoring environment 300 in FIG. 3 is not meant to imply physical or architectural limitations to the manner in which different advantageous embodiments may be implemented. Other components in addition to, and/or in place of, the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some illustrative examples, a portion or all of monitoring module 340 may be located in a remote location from vehicle 302. In this illustrative example, data 322 may be sent through a wireless communications link to a computer system at the remote location in which monitoring module 340 is located. In yet other illustrative examples, monitoring module 340 may be a hardware device that does not require number of computers 318. As another example, health monitoring system 304 may include other components in addition to computer system 314 and sensor system 316. For example, wired and wireless communications links, as well as routers and switches, also may be part of health monitoring system 304. In some illustrative examples, these types of communications links may be part of sensor system 316 depending on the particular implementation.

Figure 4:
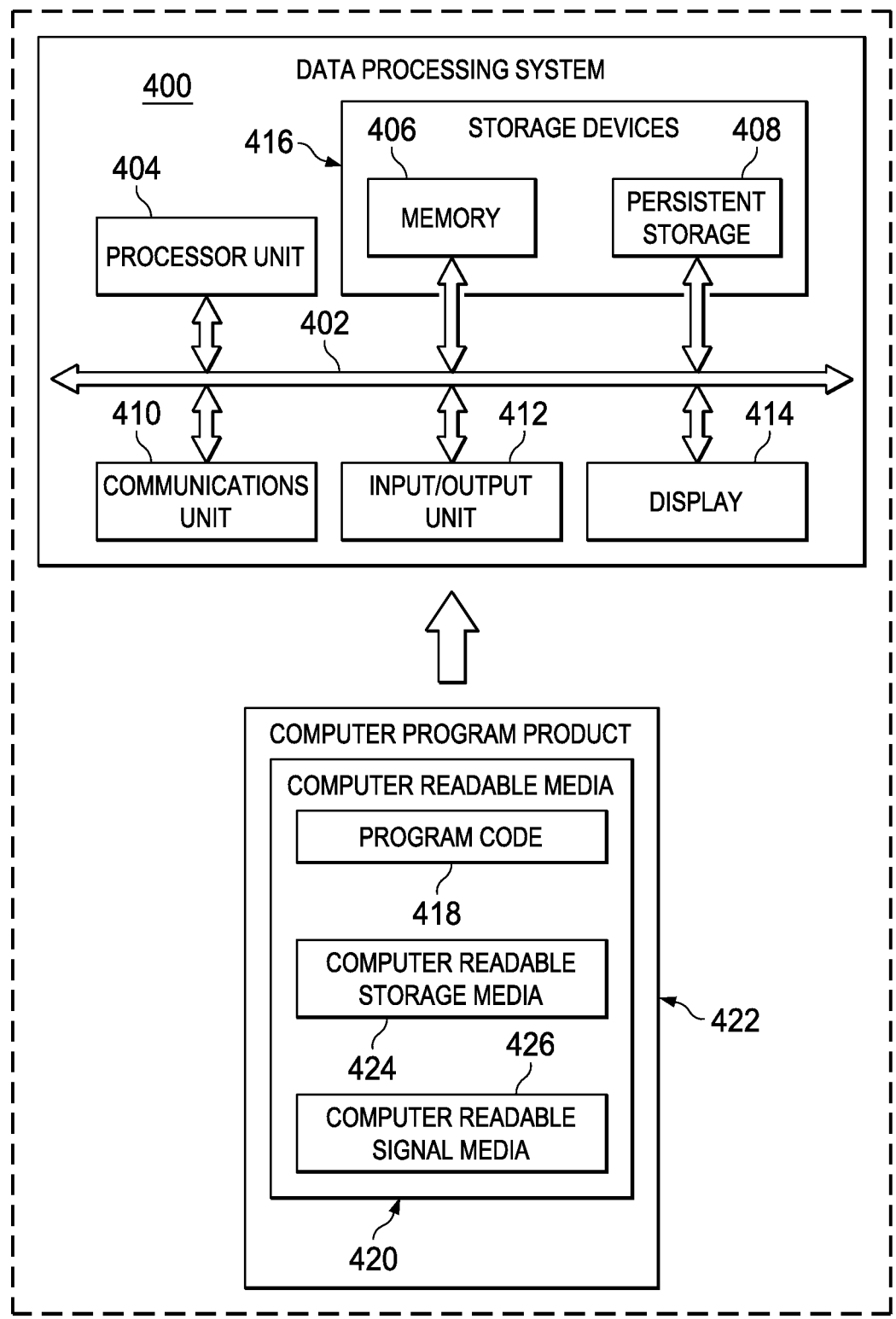
FIG. 4 is an illustration of a data processing system in accordance with an advantageous embodiment.

Turning now to FIG. 4, an illustration of a data processing system is depicted in accordance with an advantageous embodiment. In this illustrative example, data processing system 400 includes communications fabric 402, which provides communications between processor unit 404, memory 406, persistent storage 408, communications unit 410, input/output (I/O) unit 412, and display 414. Data processing system 400 is an example of a data processing system that may be used to implement number of computers 318 in computer system 314 in FIG. 3.

Processor unit 404 serves to execute instructions for software that may be loaded into memory 406. Processor unit 404 may be a number of processors, a multi-processor core, or some other type of processor, depending on the particular implementation. A number, as used herein with reference to an item, means one or more items. Further, processor unit 404 may be implemented using a number of heterogeneous processor systems in which a main processor is present with secondary processors on a single chip. As another illustrative example, processor unit 404 may be a symmetric multi-processor system containing multiple processors of the same type.

Memory 406 and persistent storage 408 are examples of storage devices 416. A storage device is any piece of hardware that is capable of storing information, such as, for example, without limitation, data, program code in functional form, and/or other suitable information either on a temporary basis and/or a permanent basis. Storage devices 416 may also be referred to as computer readable storage devices in these examples. Memory 406, in these examples, may be, for example, a random access memory or any other suitable volatile or non-volatile storage device. Persistent storage 408 may take various forms, depending on the particular implementation.

For example, persistent storage 408 may contain one or more components or devices. For example, persistent storage 408 may be a hard drive, a flash memory, a rewritable optical disk, a rewritable magnetic tape, or some combination of the above. The media used by persistent storage 408 also may be removable. For example, a removable hard drive may be used for persistent storage 408.

Communications unit 410, in these examples, provides for communications with other data processing systems or devices. In these examples, communications unit 410 is a network interface card. Communications unit 410 may provide communications through the use of either or both physical and wireless communications links.

Input/output unit 412 allows for input and output of data with other devices that may be connected to data processing system 400. For example, input/output unit 412 may provide a connection for user input through a keyboard, a mouse, and/or some other suitable input device. Further, input/output unit 412 may send output to a printer. Display 414 provides a mechanism to display information to a user.

Instructions for the operating system, applications, and/or programs may be located in storage devices 416, which are in communication with processor unit 404 through communications fabric 402. In these illustrative examples, the instructions are in a functional form on persistent storage 408. These instructions may be loaded into memory 406 for execution by processor unit 404. The processes of the different embodiments may be performed by processor unit 404 using computer implemented instructions, which may be located in a memory, such as memory 406.

These instructions are referred to as program code, computer usable program code, or computer readable program code that may be read and executed by a processor in processor unit 404. The program code in the different embodiments may be embodied on different physical or computer readable storage media, such as memory 406 or persistent storage 408.

Program code 418 is located in a functional form on computer readable media 420 that is selectively removable and may be loaded onto or transferred to data processing system 400 for execution by processor unit 404. Program code 418 and computer readable media 420 form computer program product 422 in these examples. In one example, computer readable media 420 may be computer readable storage media 424 or computer readable signal media 426.

Computer readable storage media 424 may include, for example, an optical or magnetic disk that is inserted or placed into a drive or other device that is part of persistent storage 408 for transfer onto a storage device, such as a hard drive, that is part of persistent storage 408. Computer readable storage media 424 also may take the form of a persistent storage, such as a hard drive, a thumb drive, or a flash memory, that is connected to data processing system 400. In some instances, computer readable storage media 424 may not be removable from data processing system 400. In these examples, computer readable storage media 424 is a physical or tangible storage device used to store program code 418 rather than a medium that propagates or transmits program code 418.

Computer readable storage media 424 is also referred to as a computer readable tangible storage device or a computer readable physical storage device. In other words, computer readable storage media 424 is a media that can be touched by a person.

Alternatively, program code 418 may be transferred to data processing system 400 using computer readable signal media 426. Computer readable signal media 426 may be, for example, a propagated data signal containing program code 418. For example, computer readable signal media 426 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some advantageous embodiments, program code 418 may be downloaded over a network to persistent storage 408 from another device or data processing system through computer readable signal media 426 for use within data processing system 400. For instance, program code stored in a computer readable storage medium in a server data processing system may be downloaded over a network from the server to data processing system 400. The data processing system providing program code 418 may be a server computer, a client computer, or some other device capable of storing and transmitting program code 418.

The different components illustrated for data processing system 400 are not meant to provide architectural limitations to the manner in which different embodiments may be implemented. The different advantageous embodiments may be implemented in a data processing system, including components in addition to or in place of those illustrated for data processing system 400. Other components shown in FIG. 4 can be varied from the illustrative examples shown. The different advantageous embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 404 may take the form of a hardware unit that has circuits that are manufactured or configured for a particular use. This type of hardware may perform operations without needing program code to be loaded into a memory from a storage device to be configured to perform the operations.

For example, when processor unit 404 takes the form of a hardware unit, processor unit 404 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, programmable array logic, a field programmable logic array, a field programmable gate array, and other suitable hardware devices. With this type of implementation, program code 418 may be omitted because the processes for the different embodiments are implemented in a hardware unit.

In still another illustrative example, processor unit 404 may be implemented using a combination of processors found in computers and hardware units. Processor unit 404 may have a number of hardware units and a number of processors that are configured to run program code 418. With this depicted example, some of the processes may be implemented in the number of hardware units, while other processes may be implemented in the number of processors.

In another example, a bus system may be used to implement communications fabric 402 and may be comprised of one or more buses, such as a system bus or an input/output bus. Of course, the bus system may be implemented using any suitable type of architecture that provides for a transfer of data between different components or devices attached to the bus system.

Additionally, a communications unit may include a number of devices that transmit data, receive data, or transmit and receive data. A communications unit may be, for example, a modem or a network adapter, two network adapters, or some combination thereof. Further, a memory may be, for example, memory 406, or a cache, such as found in an interface and memory controller hub that may be present in communications fabric 402.

Figure 5:
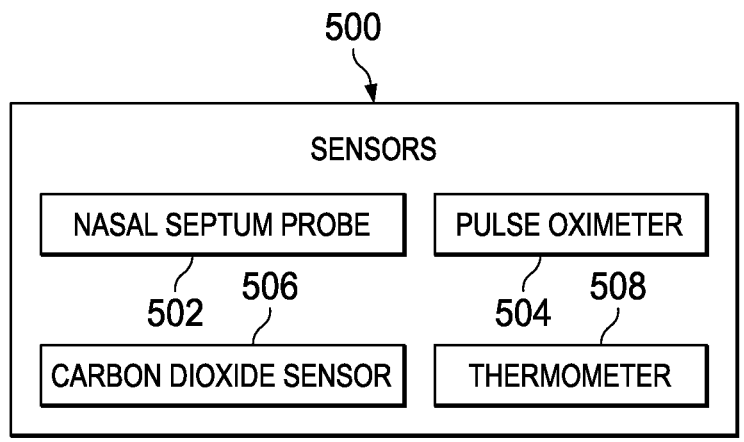
FIG. 5 is an illustration of sensors that may be used to monitor human operators in accordance with an advantageous embodiment.

With reference now to FIG. 5, an illustration of sensors that may be used to monitor human operators is depicted in accordance with an advantageous embodiment. Sensors 500 is an example of sensors within first number of sensors 326 in FIG. 3 that may be used to generate physiological data 334 for number of human operators 312.

In this illustrative example, sensors 500 include nasal septum probe 502, pulse oximeter 504, carbon dioxide sensor 506, and thermometer 508. One or more of sensors 500 may be used to obtain information for number of physiological data 334 in FIG. 3.

In this illustrative example, nasal septum probe 502 may fit over the nose bridge or septum of a human operator. In some illustrative examples, this probe may be configured for use with a face mask for an air crew member of an aircraft. Nasal septum probe 502 is used to identify blood oxygen saturation and pulse rate of the human operator in the depicted example. The blood oxygen saturation is one measure of the oxygen level in a human operator.

Pulse oximeter 504 is used to calculate blood oxygen saturation. Pulse oximeter 504 may be incorporated into a face mask, a headset, or other equipment worn by a human operator. In yet other illustrative examples, pulse oximeter 504 may be integrated into clothing such as a flight suit or uniform worn by the human operator. Pulse oximeter 504 may calculate this level of oxygen in the blood from the different rates at which oxygenated hemoglobin and reduced hemoglobin absorb light of different wavelengths of frequencies. The pulse rate may be calculated from the timing of the rise and fall of the amount of light absorbed at each wavelength in these illustrative examples.

Carbon dioxide sensor 506 measures a level of carbon dioxide in the breathing of a human operator in these examples. This sensor may be incorporated in a face mask for a human operator. Thermometer 508 may be used to measure the temperature of the human operator.

These different sensors may be associated with a human operator in a number of different ways. For example, the probes may be attached directly to the skin or other locations on the human operator. In other illustrative examples, the sensors may be integrated into clothing or equipment worn by the human operators.

The illustration of sensors 500 in FIG. 5 is not meant to imply physical or architectural limitations to the manner in which different sensors may be implemented to obtain information about vital signs for human operators. Other types of sensors may be used in addition to, or in place of, the sensors depicted in this example.

Figure 6:
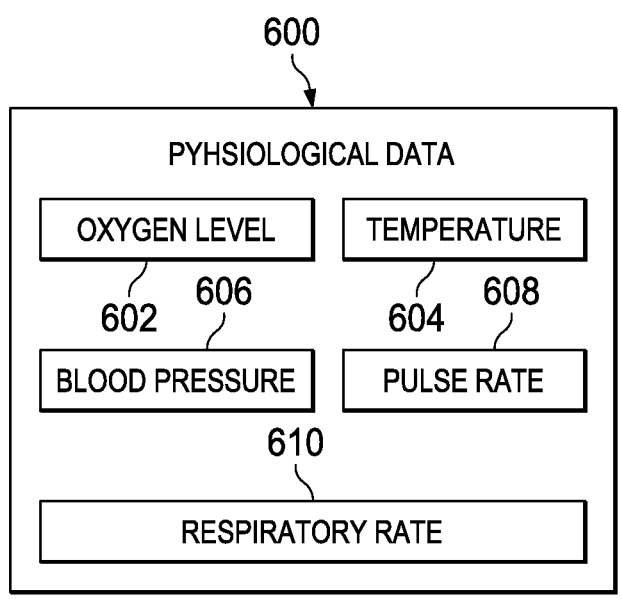
FIG. 6 is an illustration of physiological data in accordance with an advantageous embodiment.

With reference now to FIG. 6, an illustration of physiological data is depicted in accordance with an advantageous embodiment. Physiological data 600 is an example of one implementation for physiological data 334 in FIG. 3.

In this illustrative example, physiological data 600 includes oxygen level 602, temperature 604, blood pressure 606, pulse 608, and respiratory rate 610. Physiological data 600 may be measured using sensors such as sensor 500 in FIG. 5. In these illustrative examples, physiological data 600 may be used to identify whether the level of performance of a human operator is at a desired level of performance for operating the vehicle.

In one illustrative example, oxygen level 602 in the blood of a human operator may be used to determine whether a human operator is capable of performing at a desired level of performance in operating a vehicle. For example, if the oxygen level in the blood of a pilot is below a selected level, such as a threshold, the pilot may be unable to perform operations at a desired level of performance.

This desired level of performance may be determined in a number of different ways. For example, the desired level of performance may be whether the pilot can make decisions as quickly as desired, perform operations as quickly as desired, communicate with others, or other suitable types of metrics for measuring performance.

A level for oxygen level 602 at which a desired level of performance is present may be set in a number of different ways. These levels may be set using statistics based on age, sex, weight, and other suitable factors.

In other illustrative examples, the threshold level for oxygen level 602 may be set based on testing of the particular human operator. For example, a human operator may perform various operations at different oxygen levels. The results of these tests may be used to identify what oxygen level is needed for a particular human operator. The level may take different forms, such as, for example, a threshold or a range.

In addition, some operations performed by a human operator may require different oxygen levels than other operations to obtain a desired level of performance. As a result, oxygen level 602 may be different for different operations that are to be performed by the same human operator. Additionally, these levels may differ from human operator to human operator.

Other physiological data such as temperature 604, blood pressure 606, pulse rate 608, and respiratory rate 610 also may be used to identify when a desired level of performance may not be present. The different values for these levels may be set in a similar fashion as described for setting a level for oxygen level 602.

In the illustrative examples, oxygen level 602 is a value for a threshold. In the depicted examples, the value takes the form of a percentage. Of course, other types of values may be used. For example, an integer, a fraction, a rational number represented in decimal representation, or some other suitable type of value may be used. For example, the oxygen level may be in a percentage of arterial hemoglobin in the oxyhemoglobin configuration. A value that may be acceptable for a desired level of performance may be above about 95 percent. Of course, this value may vary depending on the particular human operator and/or the environment.

Physiological data 600 may be used individually or in combination with other data about other components in the vehicle to determine whether a human operator is capable of performing at a desired level of performance. In these illustrative examples, the desired level of performance may be desired level of performance 348 in FIG. 3.

The illustration of physiological data 600 in FIG. 6 is not meant to imply limitations to the manner in which vital signs may be used in the different advantageous embodiments. Other types of physiological data in addition to, or in place of, the ones illustrated in physiological data 600 may be used depending on the particular implementation.

Figure 7:
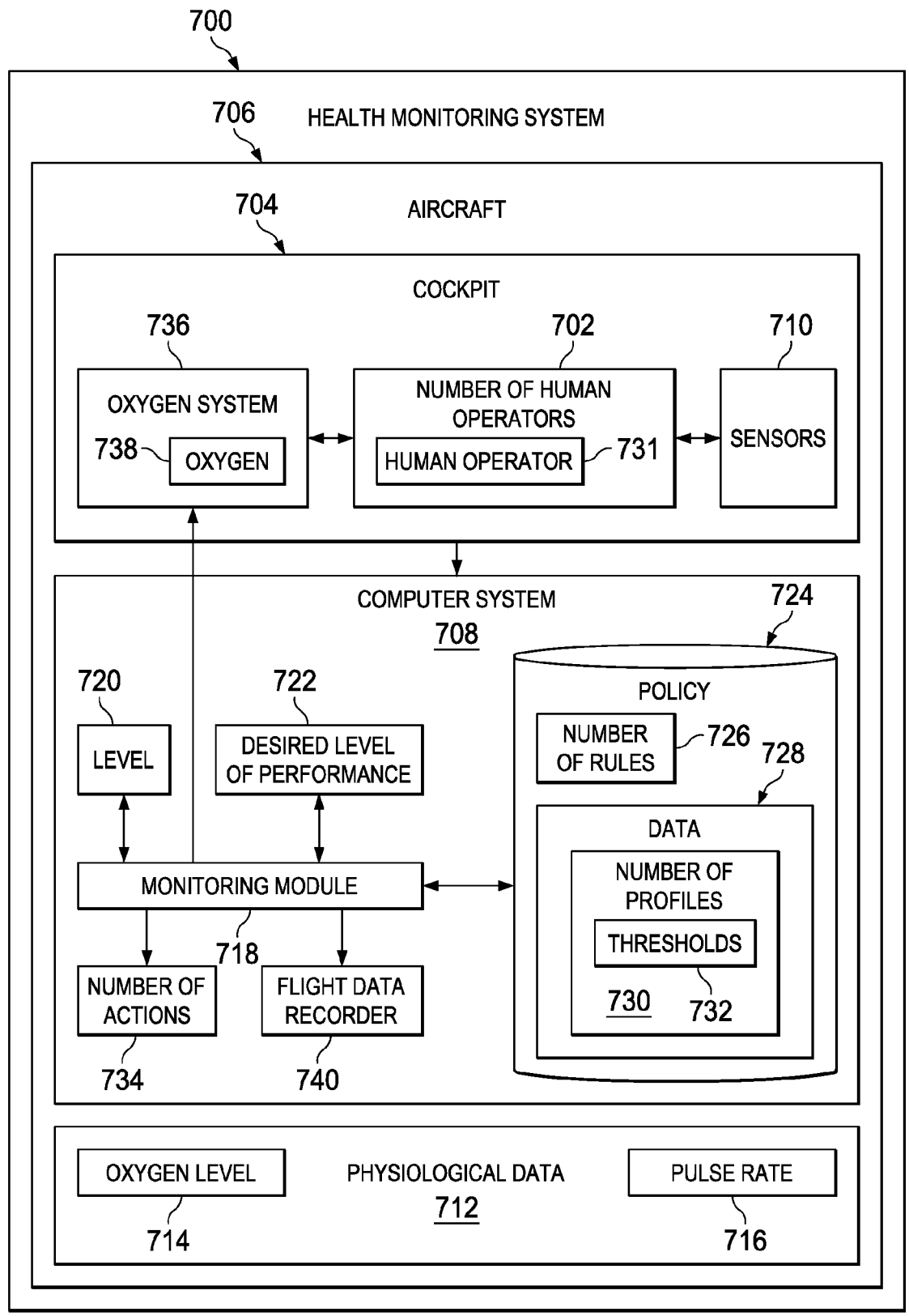
FIG. 7 is an illustration of an implementation for a health monitoring system in accordance with an advantageous embodiment.

Turning now to FIG. 7, an illustration of an implementation for a health monitoring system is depicted in accordance with an advantageous embodiment. In this illustrative example, health monitoring system 700 is an example of one implementation for health monitoring system 304 in FIG. 3.

In this illustrative example, health monitoring system 700 monitors number of human operators 702 in cockpit 704 of aircraft 706. In this illustrative example, health monitoring system 700 comprises computer system 708 and sensors 710.

Sensors 710 may be implemented using sensors to monitor number of human operators 702 to generate physiological data 712. In this particular example, physiological data 712 includes oxygen level 714 and pulse rate 716.

As depicted, monitoring module 718 in computer system 708 receives physiological data 712 from sensors 710. Monitoring module 718 determines whether physiological data 712 is within a level 720 for desired level of performance 722 for number of human operators 702. This determination is made using policy 724.

In this depicted example, policy 724 includes number of rules 726 and data 728. In these illustrative examples, data 728 may include number of profiles 730 for number of human operators 702. As a result, oxygen level 714 and pulse rate 716 are analyzed using thresholds 732 for these particular vital signs. Thresholds 732 are particular levels for oxygen level 714 and pulse rate 716 at which desired level of performance 722 is present for human operator 731 in number of human operators 702.

For example, if oxygen level 714 is less than a threshold set for oxygen level 714 in thresholds 732, monitoring module 718 may determine that human operator 731 from which those vital signs were obtained is unable to perform at a desired level of performance. In other words, that human operator 731 in number of human operators 702 may not perform operations as quickly as desired or as accurately as desired. In these examples, the threshold in thresholds 732 for oxygen level 714 may be set to identify a reduced capability to perform actions rather than an inability to perform operations in aircraft 706. A similar threshold may be set for pulse rate 716 in thresholds 732.

In these illustrative examples, each profile in number of profiles 730 may correspond to a human operator in number of human operators 702. In the different illustrative examples, each profile may be set for a particular human operator. In these illustrative examples, policy 724 may include number of profiles 730 in which each profile in number of profiles 730 corresponds to a particular human operator in number of human operators 702. Computer system 708 is configured to determine whether physiological data 712 is within level 720 of desired level of performance 722 to operate a vehicle such as aircraft 704 based on policy 724. In these illustrative examples, computer system 708 may be configured to determine whether physiological data 712 is within level 720 for desired level of performance 722 for operating the vehicle based on policy 724 in which level 720 may be for a selected user. In these illustrative examples, a selected user may be identified from a profile in number of profiles 730 in policy 724. If level 720 is not at a level for desired level of performance 722, monitoring module 718 may perform number of actions 734. In this particular example, if oxygen level 714 is lower than set in a threshold in thresholds 732, number of actions 734 includes controlling oxygen system 736 in aircraft 706 to deliver oxygen 738 to number of human operators 702.

By delivering oxygen 738 to each of number of human operators 702 with level 720 that is not within desired level of performance 722, desired level of performance 722 may be maintained in operating aircraft 706. In these illustrative examples, by delivering oxygen 738, oxygen level 714 may be increased such that oxygen level 714 meets level 720 for desired level of performance 722.

If oxygen level 714 does not reach a desired level with respect to a threshold for oxygen level 714 in thresholds 732, monitoring module 718 may then perform another action. For example, monitoring module 718 may generate an alert to indicate to other human operators in number of human operators 702 that the particular human operator is unable to perform operations at a desired level of performance. Of course, monitoring module 718 may perform other actions in addition to, or in place of, the actions depicted.

In these illustrative examples, monitoring module 718 also stores information in flight data recorder 740. Flight data recorder 740 is an example of an implementation for data recorder 354 in FIG. 3.

In these illustrative examples, monitoring module 718 may record instances when oxygen level 714 and/or pulse rate 716 do not meet thresholds 732 for desired level of performance 722 by number of human operators 702. If thresholds 732 are met, oxygen level 714 and pulse rate 716 are within a level for desired level of performance 722.

Again, in these illustrative examples, monitoring module 718 may record instances when particular human operator 731 in number of human operators 702 fails to meet, or exceed, a threshold that results in desired level of performance 722. In meeting a threshold, the value may be equal to the threshold, less than the threshold, greater than the threshold, less than or equal to the threshold, or greater than or equal to the threshold, depending on the manner in which the threshold in thresholds 732 is selected and the rule that is used in number of rules 726 and policy 724 to apply the threshold to a vital sign in physiological data 712.

Additionally, the particular value for oxygen level 714 and pulse rate 716 also may be recorded. Monitoring module 718 also may record actions taken, such as controlling oxygen system 736 to deliver oxygen 738 to number of human operators 702. In addition, data from sensors 710 also may be recorded in flight data recorder 740 when physiological data 712 fails to meet a threshold for a desired level of performance The illustration of health monitoring system 700 is an example of one implementation of health monitoring system 304 in FIG. 3 and is not meant to imply physical or architectural limitations to the manner in which health monitoring systems may be implemented in accordance with different advantageous embodiments. For example, in other advantageous embodiments, a health monitoring system may not include oxygen system 736. In yet other advantageous embodiments, health monitoring system 700 may perform actions to provide drugs or other chemicals needed to maintain a desired level of performance. For example, pills may be dispensed or injections of drugs may be applied depending on the particular implementation.

Figure 8:
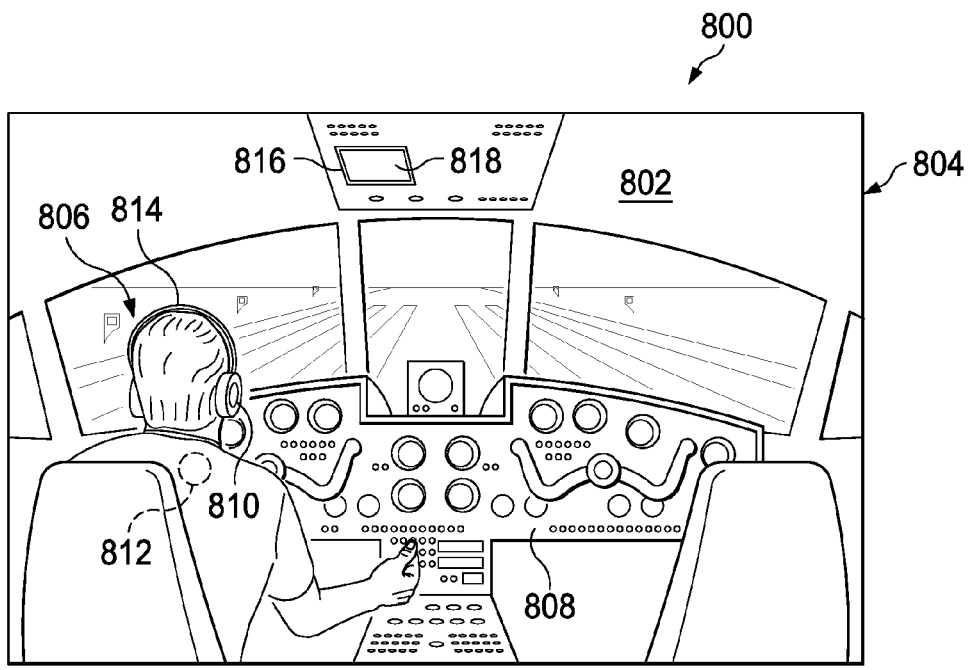
FIG. 8 is an illustration of a vehicle monitoring environment in accordance with an advantageous embodiment.

With reference now to FIG. 8, an illustration of a vehicle monitoring environment is depicted in accordance with an advantageous embodiment. In this illustrative example, vehicle monitoring environment 800 is an example of one implementation for vehicle monitoring environment 300 in FIG. 3.

In this depicted example, an illustration of cockpit 802 in aircraft 804 is shown. Cockpit 802 is an example of a component within number of components 306 in FIG. 3. For example, cockpit 802 may include structures and systems that may be monitored by a health monitoring system. Pilot 806 is an example of a human operator in number of human operators 312 for number of components 306 in FIG. 3.

In these illustrative examples, health monitoring system 700 in FIG. 7 may be implemented in cockpit 802. For example, computer system 808, sensor 810, and sensor 812 may form part of health monitoring system 700 in FIG. 7. In these illustrative examples, sensor 810 may take the form of pulse oximeter 504 and sensor 812 may take the form of thermometer 508 in FIG. 5. As depicted, sensor 810 is integrated into headset 814 worn by pilot 806.

If computer system 808 detects a level of oxygen in pilot 806 that is less than a level for a desired level of performance, oxygen system 816 may be controlled by computer system 808 to deploy an oxygen mask from compartment 818. In this illustrative example, the level is a threshold that is selected such that when the level of oxygen in the pilot is less than the threshold, desired level of performance 722 in FIG. 7 may not be present. Of course, thresholds 732 may be selected in other ways such that physiological data 712 may have a value equal to or above the threshold for desired level of performance 722 rather than less than the threshold.

Oxygen system 816 may be controlled to deploy an oxygen mask before pilot 806 is incapable of using the oxygen mask to increase the oxygen level. Of course, in other illustrative examples, control of aircraft 804 may be moved to auto pilot system 350 in FIG. 3 or remote control system 352 of aircraft 804 may be performed by another human operator at a remote location.

Figure 9:
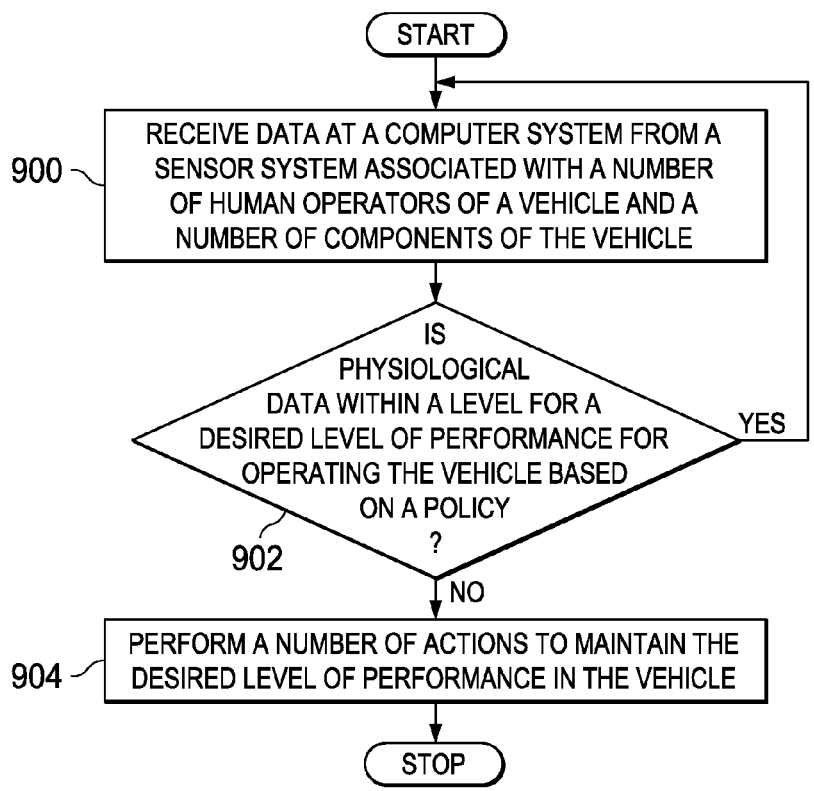
FIG. 9 is a flowchart of a process for monitoring a vehicle in accordance with an advantageous embodiment.

With reference now to FIG. 9, a flowchart of a process for monitoring a vehicle is depicted in accordance with an advantageous embodiment. In this illustrative example, the process in FIG. 9 may be implemented in vehicle monitoring environment 300 in FIG. 3. In particular, the process illustrated in this flowchart may be implemented within monitoring module 340 in FIG. 3.

The process in FIG. 9 identifies operations for monitoring human operators in a vehicle. Human operators may be considered components of a vehicle in addition to other components, such as structures and systems.

The process begins by receiving data at a computer system from a sensor system associated with a number of human operators of a vehicle and a number of components of the vehicle (operation 900). In operation 900, data is received to identify the health of both the number of human operators and number of components in the vehicle. In other words, this data may be used to identify the number of human operators as they operate the vehicle in addition to identifying the health of the number of components.

Thereafter, a determination is made as to whether the physiological data is within a level for a desired level of performance for operating the vehicle based on a policy (operation 902).

If the physiological data is within the level, the process returns to operation 900 to receive additional physiological data. Otherwise, the process performs a number of actions to maintain the desired level of performance in the vehicle (operation 904) with the process terminating thereafter. The number of actions may take various forms depending on the particular implementation and the particular type of physiological data being measured. Actions may include ones to change the physiological data such that the level identified for the physiological data is within a level for a desired level of performance for operating the vehicle.

Figure 10:
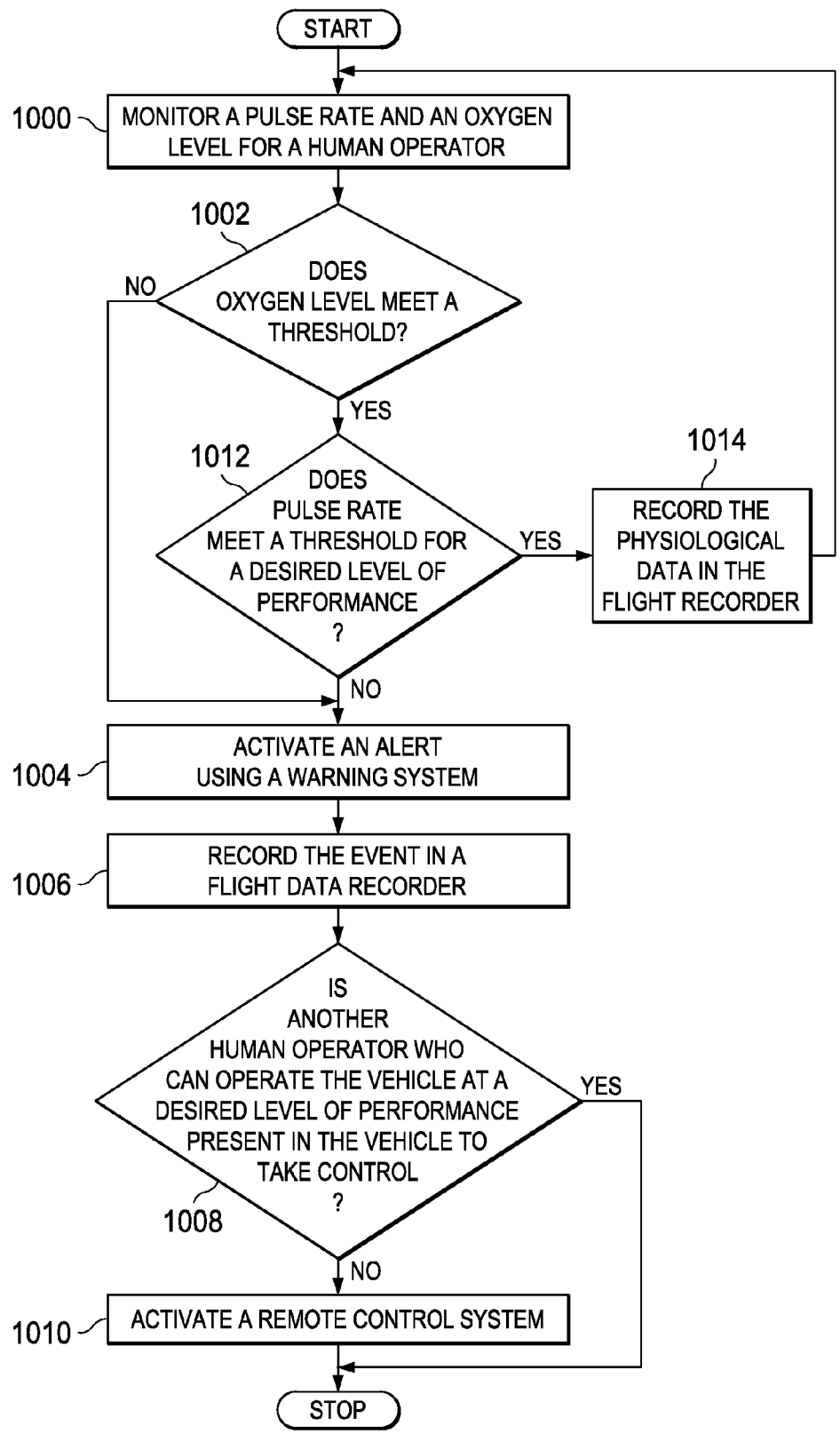
FIG. 10 is a flowchart of a process for monitoring a human operator in accordance with an advantageous embodiment.

With reference now to FIG. 10, a flowchart of a process for monitoring a human operator is depicted in accordance with an advantageous embodiment. The process illustrated in FIG. 10 may be implemented in vehicle monitoring environment 300 in FIG. 3. In particular, the process may be implemented in a health monitoring system such as health monitoring system 304 or health monitoring system 700 in FIG. 7. In these illustrative examples, the different operations may be performed by monitoring module 340 in FIG. 3 or monitoring module 718 in FIG. 7.

The process begins by monitoring a pulse rate and an oxygen level for a human operator (operation 1000). Monitoring of the pulse rate and oxygen level may be performed using a sensor. In these illustrative examples, the sensor may be, for example, without limitation, nasal septum probe 502 and/or pulse oximeter 504 in FIG. 5.

If pulse oximeter 504 is used, the sensor may be a clip-on sensor that is attached to the earlobe of the human operator. This type of sensor is configured to generate data about pulse rates and oxygen levels in the human operator. Of course, in other illustrative examples, this sensor may be incorporated into equipment worn by the human operator. For example, the sensor may be incorporated into a headset or face mask worn by the human operator.

A determination is made as to whether the oxygen level meets a threshold (operation 1002). By meeting a threshold, the value for the oxygen level may be less than the threshold, greater than the threshold, less than or equal to the threshold, greater than or equal to the threshold, equal to the threshold, or some combination thereof. Whether a value is required to be above or below or equal to the threshold is determined by the manner in which the threshold is set. For example, if the threshold for an oxygen level is from about 95 percent to about 100 percent, the threshold may be set at about 95 percent. If the oxygen level of the human operator is less than about 95 percent, then the oxygen level does not meet the threshold in this example. If the threshold is met, the oxygen level has a value that is within a level for a desired level of performance in these depicted examples.

If the oxygen level does not meet a threshold, the process activates an alert using a warning system (operation 1004). The alert may be, for example, a sound, a flashing light, and/or some other suitable type of alert. This warning may be viewed by other human operators or other personnel in the vehicle and/or in a remote location.

The process records the event in a flight data recorder (operation 1006). The events may include an identification of the human operator, the oxygen level, the pulse rate, and the alert generated.

A determination is then made as to whether another human operator who can operate the vehicle at a desired level of performance is present in the vehicle to take control (operation 1008). If another human operator who can operate the vehicle at a desired level of performance is unable to take control present in the vehicle to take control, the process may activate a remote control system (operation 1010) with the process terminating thereafter. At this point, another human operator or computer system may remotely control the aircraft.

With reference again to operation 1008, if another human operator is present in the aircraft that can operate the vehicle with a desired level of performance, the process terminates because no other action is needed by the monitoring module.

With reference again to operation 1002, if the oxygen level meets the threshold for a desired level of performance, the process determines whether the pulse rate meets the threshold for a desired level of performance (operation 1012). If the pulse rate does not meet the threshold, the process proceeds to operation 1004 as described above. Otherwise, the process records the physiological data in the flight recorder (operation 1014) with the process then returning to operation 1000 as described above. In this illustrative example, physiological data, such as the oxygen level and pulse rate for a particular human operator, is recorded in the flight data recorder even when the values for these types of data meet the thresholds to have a level that meets a desired level of performance.

Figure 11:
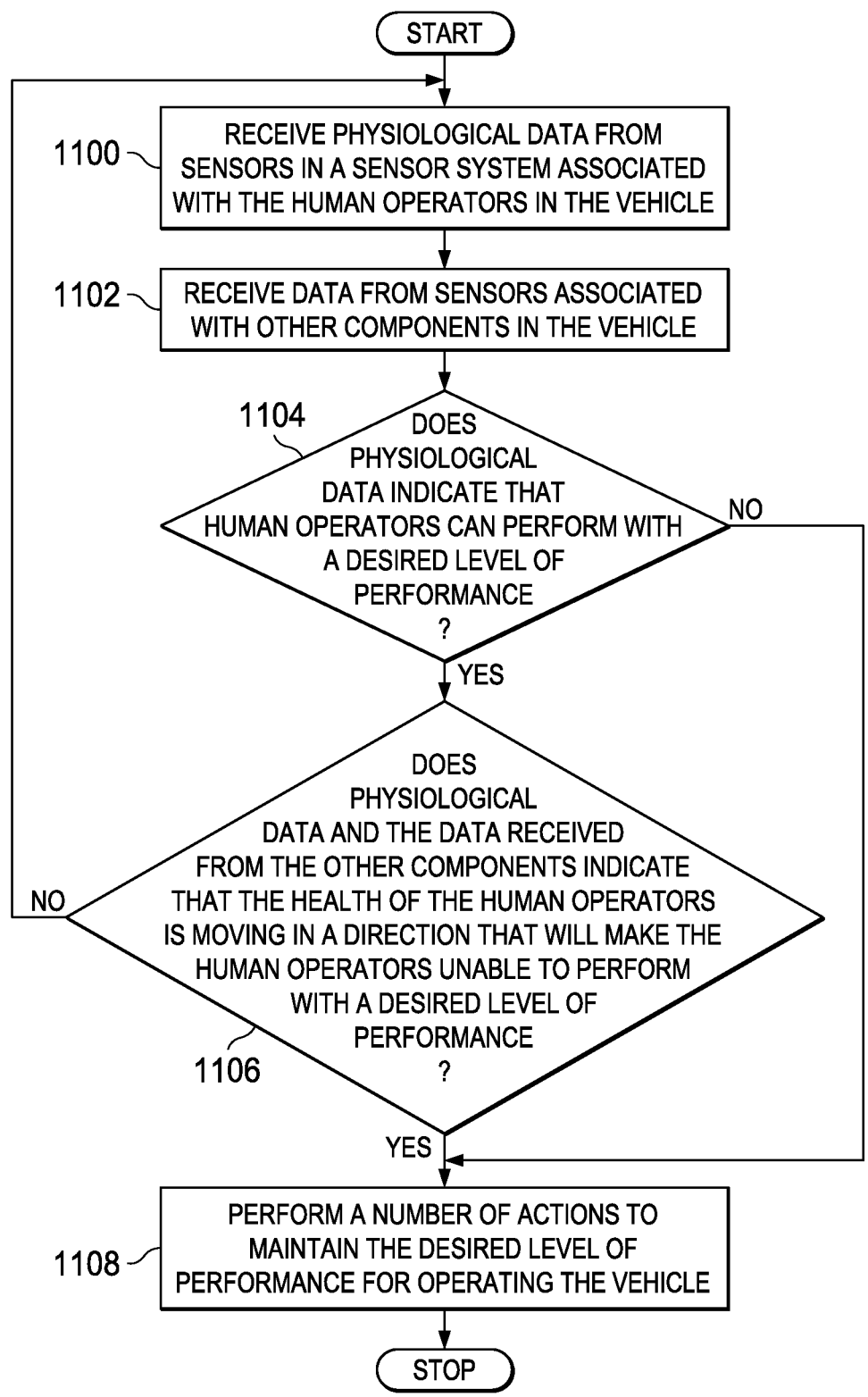
FIG. 11 is a flowchart for monitoring human operators of a vehicle in accordance with an advantageous embodiment.

With reference now to FIG. 11, a flowchart for monitoring human operators of a vehicle is depicted in accordance with an advantageous embodiment. The process illustrated in FIG. 11 may be implemented in vehicle monitoring environment 300 in FIG. 3. In particular, the process may be implemented in a health monitoring system such as health monitoring system 304 or health monitoring system 700 in FIG. 7. In these illustrative examples, the different operations may be performed by monitoring module 340 in FIG. 3 or monitoring module 718 in FIG. 7.

The process begins by receiving physiological data from sensors in a sensor system associated with the human operators in the vehicle (operation 1100). The process also receives data from sensors associated with other components in the vehicle (operation 1102). A determination is made as to whether the physiological data indicates that human operators can perform with a desired level of performance (operation 1104). In these examples, the determination in operation 1104 may be made by determining whether the physiological data meets a level identified for a desired level of performance for the physiological data. Depending on the types of physiological data, multiple thresholds may be present for the different types of physiological data.

In these examples, a requirement may be present for some or all of the thresholds to be met for the level of the physiological data to meet the desired level of performance. For example, with a pulse rate and oxygen rate, a pulse rate of some number of pulses per minute and a percentage of oxygen in the blood may both be required for the level to meet the level of performance. In other examples, the temperature of the pilot also may be in the physiological data. This particular type of physiological data may be omitted in determining whether the level of the physiological data meets the desired level of performance.

If the physiological data indicates that the human operators can perform with a desired level of performance, a determination is made as to whether the physiological data and the data received from the other components indicate that the health of the human operators is moving in a direction that will make the human operators unable to perform with a desired level of performance (operation 1106).

If the physiological data and the data from the other components indicate that the human operators will be unable to perform operations within a desired level of performance, the process then performs a number of actions to maintain the desired level of performance for operating the vehicle (operation 1108) with the process terminating thereafter.

With reference again to operation 1104, if the physiological data indicates that the human operators is unable to perform at a desired level of performance, the process also proceeds to operation 1108 as described above.

In a similar fashion, in operation 1106, if the physiological data and the data from the other components does not indicate the human operators will be unable to perform operations at the desired level of performance, the process returns to operation 1100 as described above.

In operation 1106, physiological data and data from sensors associated with other components in the vehicle are used to determine whether a condition is present that will cause the human operator to be unable to perform at a desired level of performance. For example, if the blood oxygen level is identified as decreasing, the blood oxygen level may not be at a level that indicates that the human operator is unable to perform at a desired level of performance. However, data such as, for example, carbon dioxide levels or carbon monoxide levels in a cockpit or cabin may be increasing. This increase may reach a threshold that indicates that the human operator will continue to have a reduction in the oxygen level that will reach a level such that the human operator is unable to perform operations within a desired level of performance.

In this manner, both physiological data about the human operator and data from sensors monitoring other components in the vehicle may be used to determine if other operations are needed to maintain a desired level of performance in operating the vehicle. These operations may include, for example, activating an oxygen system, generating an alert to allow another human operator to take control, activating a remote control system to allow remote operation of the vehicle, setting an auto-pilot to automatically direct the vehicle to a desired location, and/or some other suitable type of operation.

Figure 12:
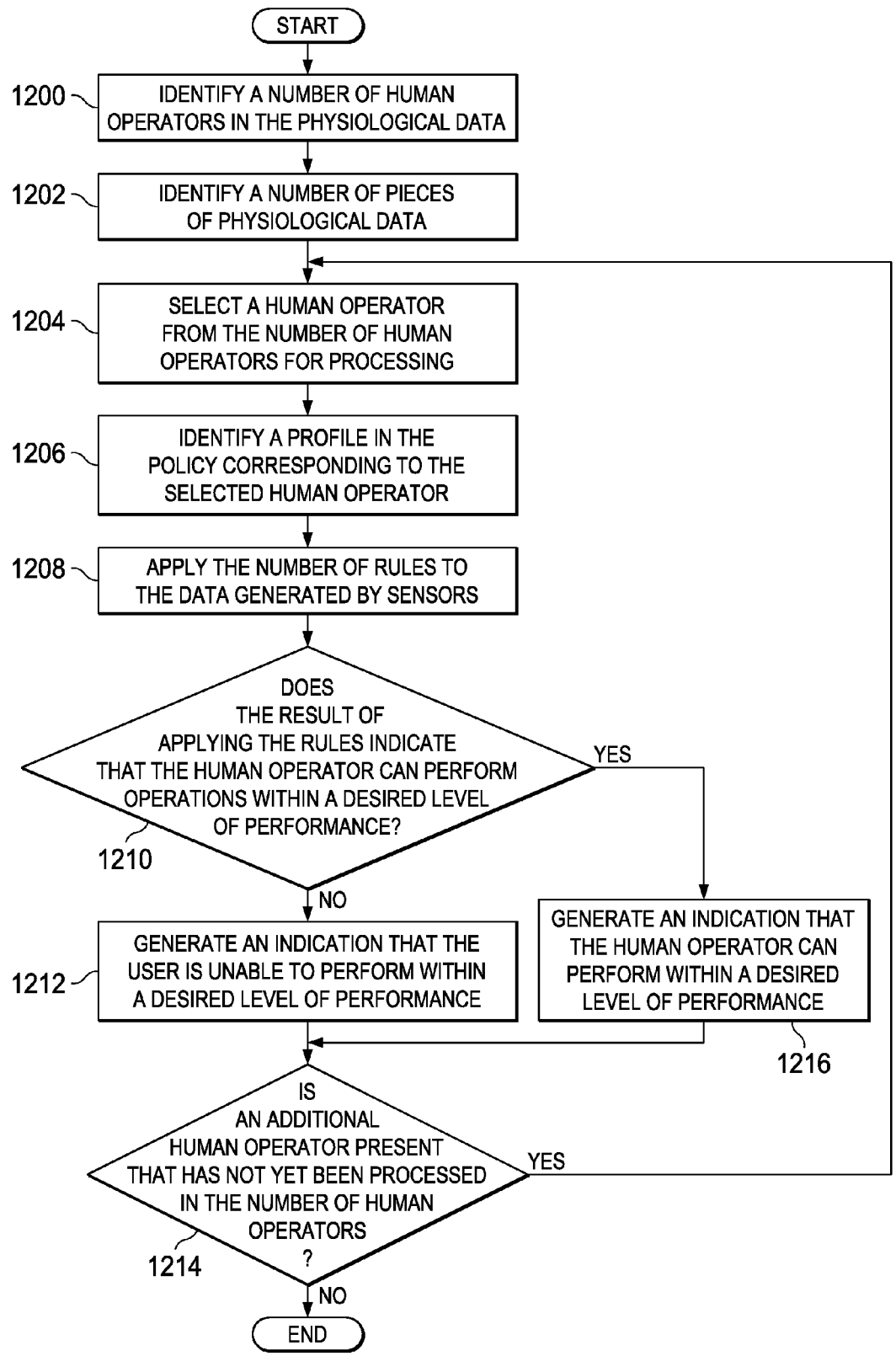
FIG. 12 is a flowchart of a process for processing physiological data using profiles in accordance with an advantageous embodiment.

With reference now to FIG. 12, a flowchart of a process for processing physiological data using profiles is depicted in accordance with an advantageous embodiment. The process illustrated in FIG. 12 is an example of one implementation for operation 902 in FIG. 9 and operation 1104 and operation 1106 in FIG. 11.

The process begins by identifying a number of human operators in the physiological data (operation 1200). In operation 1200, the identification of the number of human operators may be made in a number of different ways. For example, the physiological data received from sensors may have identifiers that are associated with particular human operators. These identifiers are unique in these examples and may be numbers, numbers and letters, or other suitable types of identifiers.

For example, physiological data containing oxygen levels may have an identifier that corresponds to a particular human operator. The oxygen level for another human operator may have another identifier. In this manner, physiological data may be identified for different human operators when more than one human operator is present in the number of human operators.

The process then identifies a number of pieces of physiological data (operation 1202). The number of pieces of physiological data may be of the same type or a different type. The different types of physiological data include, for example, those illustrated in physiological data 600 in FIG. 6. For example, the physiological data may include oxygen levels and pulse rates. In these illustrative examples, each piece of physiological data may contain a value for one type of physiological data. For example, a value of 90 percent for an oxygen level may be one piece of physiological data, a value of 94 percent for the oxygen level may be a second piece of physiological data, and a value of 75 heart beats per minute for a pulse rate may be a third piece of physiological data.

The process then selects a human operator from the number of human operators for processing (operation 1204). The process then identifies a profile in the policy corresponding to the selected human operator (operation 1206). In these illustrative examples, each human operator has a profile that corresponds to the human operator. This profile may be a profile in number of profiles 730 in data 728 for policy 724 in FIG. 7.

The profile includes a level needed for the physiological data to indicate that a desired level of performance is present for the human operator. A level may include one or more thresholds for one or more pieces of physiological data. In these examples, the pieces may be for different types of physiological data.

Additionally, in some illustrative examples, the level may include other types of comparisons, such as a range or other types of values for use in applying the number of rules in the policy to the physiological data.

The process then applies the number of rules to the data generated by sensors (operation 1208). In some cases, the rules are only applied to the physiological data. In other cases, the rules may also be applied to data from sensors monitoring other components such as structures or systems.

A determination is made as to whether the result of applying the rules indicates that the human operator can perform operations within a desired level of performance (operation 1210). This indication may be made based on whether the physiological data indicates that the human operator is currently capable of performing with a desired level of performance. Further, this determination also may include a determination as to whether the data indicates that the health of the human operator is moving toward or away from inability to perform within a desired level of performance.

If the information indicates that the human operator has a health level that is moving away from a desired level of performance, the determination may be that the human operator is unable to perform with a desired level of performance because of the change in the level. In other words, trends away from a desired level of performance also may be identified as, for example, ones where the human operator will soon be unable to perform within the desired level of performance in these illustrative examples.

If the human operator is unable to perform within a desired level of performance, the process generates an indication that the user is unable to perform within a desired level of performance (operation 1212). The process then determines whether an additional human operator is present that has not yet been processed in the number of human operators (operation 1214). If an additional human operator is present, the process then returns to operation 1204 to select another human operator for processing. Otherwise, the process terminates.

With reference again to operation 1210, if the application of the rules indicates that the human operator is capable of performing operations with a desired level of performance, an indication is generated to indicate that the human operator can perform within a desired level of performance (operation 1216). The process then proceeds to operation 1214 as discussed above.

The flowcharts and block diagrams in the different depicted embodiments illustrate the architecture, functionality, and operation of some possible implementations of apparatus and methods in different advantageous embodiments. In this regard, each block in the flowchart or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved. Also, other blocks may be added in addition to the illustrated blocks in a flowchart or block diagram.

Thus, the different advantageous embodiments provide a method and apparatus for monitoring a vehicle. In the different advantageous embodiments, a health monitoring system may comprise a sensor system and a computer system. The sensor system is associated with the number of human operators of the vehicle and a number of components in the vehicle. The sensors system is configured to generate physiological data for the number of human operators. The computer system is connected to the number of sensors and is configured to receive the physiological data to determine whether physiological data is within a desired level of performance for operating the vehicle based on the policy. The computer system is configured to perform a number of actions to maintain a desired level of performance in operating the vehicle in response to the physiological data not being within the level for the desired level of performance.

The different advantageous embodiments provide a capability to perform operations to maintain a desired level of performance in operating the vehicle. The desired level of performance in these examples may be by returning the human operator to a physiological condition that allows for the desired level of performance. The desired level of performance may be performed by changing control of the vehicle to another human operator, to a control system, and/or some other suitable type of operation. With one or more of the different advantageous embodiments, a capability to monitor all components in the vehicle, including human operators, may be performed. Further, with this type of monitoring, operations may be taken to maintain a desired level of performance for the vehicle. In some examples, the desired level of performance may be to land an aircraft at a predetermined location, remotely control aircraft, or some other suitable type of operation.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus, comprising:
   a first sensor system configured to be associated with a number of human operators of a vehicle, configured to generate physiological data for the number of human operators, and configured to generate environment data for the environment around the number of human operators in the vehicle corresponding to a number of physiological data, the first sensor system including at least an oximeter positioned in a headset of at least one human operator;
   a second sensor system configured to be associated with a number of components in the vehicle and configured to generate data about the number of components in the vehicle, the number of components comprising a number of structures and a number of systems, the first sensor system different from the second sensor system; and
   a computer system in communications with the sensor system, the computer system:
      configured to receive the physiological data from the first sensor system;
      configured to receive data about the number of components for the vehicle from the second sensor system;

configured to determine whether first physiological data for a first human operator meets a threshold for operating the vehicle based on a policy, the policy based on a specific profile for the first human operator and the specific profile selected from a number of profiles in which each profile in the number of profiles corresponds to a particular human operator in the number of human operators;

configured to perform a first number of actions to maintain a desired level of performance for operating the vehicle in response to the first physiological data not meeting the threshold, the first number of actions including at least providing oxygen to at least a first human operator;

configured to determine whether second physiological data for the first human operator meets the threshold for operating the vehicle based on the policy after the first number of actions has been performed; and configured to perform a second number of actions if the second physiological data is not within the desired level after the first number of actions, the second number of actions including at least generating an alert to a second human operator;

wherein the first physiological data indicates that health of the first human operator is moving in a direction that will make the first human operator unable to perform with the desired level of performance.

2. The apparatus of claim 1, wherein the second sensor system gathers data regarding at least a temperature and a pressure associated with the vehicle, and the first sensor system is configured to determine whether the physiological data and the data about the number of components for the vehicle indicate that the desired level of performance for operating the vehicle cannot be maintained by the number of human operators; and configured to perform the number of actions to maintain the desired level of performance for operating the vehicle in response to the determination that the desired level of performance for operating the vehicle cannot be maintained by the number of operators.

3. The apparatus of claim 1 further comprising:

an oxygen system configured to deliver oxygen to the number of human operators of the vehicle;

wherein a first data about the number of physiological data comprises a level of the oxygen in the blood for at least one of the number of human operators; and wherein in being configured to perform the number of actions when the number of physiological data is not within the level for the desired level of performance to operate the vehicle in a desired manner, the computer system is configured to control the oxygen system to deliver the oxygen to at least each of the number of human operators in which the number of physiological data is not within the level for the desired level of performance.

4. The apparatus of claim 1, wherein the number of actions comprises at least one of:

changing control of the vehicle to an autopilot system, changing the control of the vehicle to a remote location, generating an alert, and controlling an oxygen system to deliver the oxygen to the number of human operators.

5. The apparatus of claim 1, wherein the policy includes a number of profiles in which each profile in the number of profiles corresponds to a particular human operator in the number of human operators; and wherein in being configured to determine whether the physiological data is within the level for the desired level of performance for operating the vehicle based on the policy, the computer system is configured to determine whether the physiological data is within the level for the desired level of performance for operating the vehicle based on the policy in which the level for a selected user is identified from the profile for the selected user in the policy.

6. The apparatus of claim 1, wherein the sensor system comprises a carbon monoxide sensor and a number of sensors selected from at least one of a pulse oximeter, a nasal septum probe, a carbon dioxide sensor, and a thermometer.

7. The apparatus of claim 1, wherein the physiological data comprises an oxygen level and a pulse rate.

8. The apparatus of claim 1 further comprising the vehicle.

9. The apparatus of claim 8, wherein the vehicle is selected from one of a submarine, a personnel carrier, a tank, a train, an automobile, a bus, a spacecraft, and a surface ship.

10. The apparatus of claim 2, wherein the second sensor system is configured to determine a position for the number of components.

11. The apparatus of claim 10, wherein the second sensor system further determines a load on a component and a response by a component to a command.

12. The apparatus of claim 5, wherein each human operator has a profile that corresponds to the human operator;

wherein a threshold level for an oxygen level for each human operator of the number of human operators may be set based on each human operator that identify a particular oxygen level needed for each human operator to perform various operations; and wherein the oxygen level may be different for different operations that are to be performed by a same human operator.

13. The apparatus of claim 1, wherein the vehicle is a pressurized aircraft.

14. The apparatus of claim 1, wherein a sensor of the sensor system is integrated into a headset worn by a human operator of the number of human operators.

15. The apparatus of claim 1, wherein the oxygen system is configured to deploy an oxygen mask before a human operator of the number of human operators is incapable of using the oxygen mask to increase the oxygen level.

16. The apparatus of claim 1, wherein when the physiological data of a first human operator of the number of human operators does not meet the level for the desired level of performance, the computer system is configured to determine whether a second human operator of the number of human operators can operate the vehicle at the desired level of performance is present in the vehicle;

wherein when the second human operator is determined to be present, the computer system is configured to take no action and allow the second human operator to control the vehicle.

17. The apparatus of claim 1, wherein the computer system is configured to record the physiological data in a flight recorder.

18. A health monitoring system for an aircraft, the system comprising:

a first sensor system associated with a number of human operators of the aircraft, wherein the first sensor system is configured to generate physiological data for the number of human operators and data for an environment in which the number of human operators are present, the data for the environment including at least carbon monoxide, and the first sensor system including at least an oximeter positioned in a headset of at least one human operator;

a second sensor system associated with a number of components in the aircraft and configured to generate data for the number of components, the data including at least a temperature and a pressure associated with the number of components, the number of components comprising a number of structures and a number of systems, the first sensor system different from the second sensor system; and a computer system connected to the first sensor system and the second sensor system, wherein the computer system is configured to receive the physiological data, the data from the environment, and the data from the number of components;

determine whether first physiological data of a first human operator in the number of human operators meets a threshold for operating the aircraft based on a profile for the human operator in a number of profiles in which each profile in the number of profiles corresponds to a particular human operator in the number of human operators, the number of profiles at least oxygen level and heart rate for the number of human operators;

perform a number of actions to maintain a desired level of performance for operating the aircraft in response to the first physiological data not meeting the threshold, the first number of actions including at least providing oxygen to at least the first human operator;

determine whether second physiological data for the first human operator meets the threshold for operating the vehicle based on the policy after the first number of actions has been performed; and perform a second number of actions if the second physiological data is not within the desired level after the first number of actions, the second number of actions including at least generating an alert to a second human operator;

wherein the first physiological data indicates that health of the first human operator is moving in a direction that will make the first human operator unable to perform with the desired level of performance.

19. The health monitoring system of claim 18, wherein the first sensor system comprises a number of sensors selected from at least one of a pulse oximeter, a nasal septum probe, a carbon dioxide sensor, and a thermometer.

20. A method for monitoring a vehicle, the method comprising:

receiving, at a computer system, physiological data and data about an environment from a first sensor system associated with a number of human operators of the vehicle and the environment in which the number of human operators are positioned, the first sensor system including at least an oximeter positioned in a headset of at least one human operator, wherein the physiological data includes a number of physiological data for the number of human operators including at least an oxygen level and the data from the environment includes at least a carbon monoxide level;

receiving at the computer system data about a number of components in the vehicle, the data about the number of components including temperature, pressure, and position data, the number of components comprising a number of structures and a number of systems, the first sensor system different from the second sensor system;

determining, by the computer system, whether first physiological data meets a threshold for operating the vehicle based on a policy, the policy based on a specific profile for a first human operator;

performing, by the computer system, a first number of actions to maintain a desired level of performance for operating the vehicle in response to the first physiological data not meeting the threshold, the first number of actions including at least providing oxygen to at least the first human operator;

determining, by the computer system, whether second physiological data for the first human operator meets the threshold for operating the vehicle based on the policy after the first number of actions has been performed; and performing, by the computer system, a second number of actions if the second physiological data is not within the desired level after the first number of actions, the second number of actions including at least generating an alert to a second human operator;

wherein the first physiological data indicates that health of the first human operator is moving in a direction that will make the first human operator unable to perform with the desired level of performance.

21. The method of claim 20 further comprising:

determining, by the computer system, whether the physiological data and the data about the number of components for the vehicle indicate that the desired level of performance for operating the vehicle cannot be maintained by the number of human operators; and performing the number of actions to maintain the desired level of performance for operating the vehicle in response to the determination that the desired level of performance for operating the vehicle cannot be maintained by the number of operators;

wherein performing, by the computer system, the number of actions to maintain the desired level of performance for operating the vehicle in response to the number of physiological data not being within the level for the desired level of performance comprises:

controlling an oxygen system in the vehicle to deliver oxygen to at least each of the number of human operators in which the number of physiological data is not within the level for the desired level of performance;

wherein the number of actions comprises at least one of changing control of the vehicle to an autopilot, changing the control of the vehicle to a remote location, generating an alert, and controlling an oxygen system to deliver oxygen to the number of human operators;

wherein the policy includes a number of profiles in which each profile in the number of profiles corresponds to a particular human operator in the number of human operators and wherein determining whether the physiological data is within the level for the desired level of performance for operating the vehicle based on the policy comprises:

determining whether the physiological data is within the level for the desired level of performance for operating the vehicle based on the policy in which the level for a selected human operator in the number of human operators is identified from the profile for the selected human operator in the policy;

wherein the sensor system comprises a number of sensors selected from at least one of a pulse oximeter, a nasal septum probe, a carbon dioxide sensor, and a thermometer;
wherein the physiological data comprises an oxygen level and a pulse rate; and
wherein the vehicle is selected from one of a submarine, a personnel carrier, a tank, a train, an automobile, a bus, a spacecraft, and a surface ship.

* * * * *